United States Patent [19]

Cooper et al.

[11] Patent Number: 4,482,553
[45] Date of Patent: Nov. 13, 1984

[54] BENZOTHIENYLGLYCYL CEPHALOSPORIN DERIVATIVES

[75] Inventors: Robin D. G. Cooper; Bernard J. Graves; Edward R. Lavagnino, all of Indianapolis, Ind.

[73] Assignee: Eli Lilly and Company, Indianapolis, Ind.

[21] Appl. No.: 484,126

[22] Filed: Apr. 12, 1983

[51] Int. Cl.$^3$ ............... A61K 31/545; C07D 501/22; C07D 501/57
[52] U.S. Cl. ..................... 424/246; 544/21; 544/22; 544/28; 549/58
[58] Field of Search ............ 424/246; 544/28, 21, 544/22

[56] References Cited

U.S. PATENT DOCUMENTS 3,575,969  4/1971  Morin et al. ............ 544/28
4,024,133  5/1977  Cook et al. ............ 544/28

Primary Examiner—Paul M. Coughlan, Jr.
Attorney, Agent, or Firm—Charles W. Ashbrook; Arthur R. Whale

[57] ABSTRACT 7-(2-Benzothienyl)glycylamido cephalosporins have good gram positive activity and favorable pharmacokinetics and are orally effective.

20 Claims, No Drawings

BENZOTHIENYLGLYCYL CEPHALOSPORIN DERIVATIVES

BACKGROUND OF THE INVENTION

The cephalosporin class of antibiotics has been extensively studied, and several members of the class are now routinely used to combat bacterial diseases caused by a broad spectrum of gram positive and gram negative microorganisms. The majority of such compounds are not effective orally, but rather are administered intramuscularly or intravenously, thus necessitating assistance from medically trained personnel. Moreover, since the compounds are effective against a broad spectrum of microorganisms, they generally are not employed for their specificity.

There remains a need for cephalosporin antibiotics that are orally effective and have a degree of specificity toward one or more groups of microorganisms. An object of this invention is to provide a group of compounds that satisfy these needs.

SUMMARY OF THE INVENTION

This invention concerns cephalosporin antibiotics. The invention is more particularly directed to a group of (2-benzothienyl)glycylamido cephalosporin derivatives having the formula

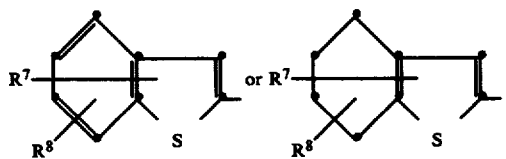

wherein $R^1$ is

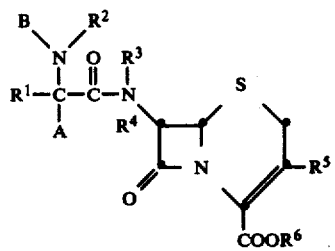

in which $R^7$ and $R^8$ independently are hydrogen, halo, hydroxy, $C_1$-$C_4$-alkyl, $C_1$-$C_4$ alkoxy, nitro, amino, $C_1$-$C_4$ alkanoylamino, $C_1$-$C_4$ alkylsulfonylamino, and when $R^7$ and $R^8$ are on adjacent carbon atoms, they can be taken together to form methylenedioxy; provided that at least one of $R^7$ and $R^8$ is other than hydrogen;

A and B both are hydrogen, or taken together complete a double bond;

$R^2$ is hydrogen, an amino protecting group, hydroxy, or methoxy, and $R^3$ is hydrogen, or $R^2$ and $R^3$ taken together are

where

M and N independently are $C_1$-$C_4$ alkyl;

$R^4$ is hydrogen, methoxy or methylthio;

$R^5$ is hydrogen, methoxy, methyl, halo, methoxymethyl, or vinyl;

$R^6$ is hydrogen, a salt forming cation group, or a carboxy protecting group; and the pharmaceutically acceptable acid addition salts thereof; with the proviso that $R^2$ is hydroxy or methoxy only when A and B complete a double bond, and that A and B both are hydrogen when $R_3$ is other than hydrogen.

Preferred compounds provided by the invention include those of the above formula wherein $R^1$ is

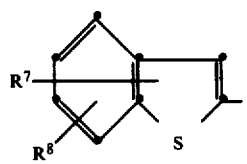

and $R^7$ and $R^8$ are as defined above. Within this group, preferred compounds include those wherein $R^2$ is hydrogen, an amino protecting group, hydroxy or methoxy, and $R^6$ is hydrogen or a carboxy protecting group.

Another preferred group of compounds are those wherein $R^1$ is

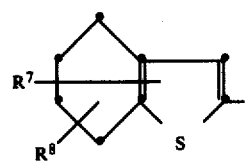

and $R^7$ and $R^8$ are as defined above. Especially preferred compounds within this group include those wherein A, B, $R^2$, $R^3$, $R^4$ and $R^6$ all are hydrogen.

A particularly preferred group of compounds provided by this invention are defined by the formula

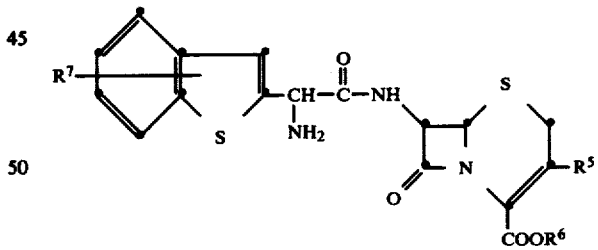

wherein $R^5$, $R^6$ and $R^7$ are as defined above. The most preferred compounds are those within this group wherein $R^7$ is halo, hydroxy or methoxy, $R^5$ is methyl or chloro, and $R^6$ is hydrogen or a salt forming group such as sodium or potassium cation.

An additional embodiment of this invention is a pharmaceutical formulation comprising a benzothienylglycylamido cephalosporin derivative as defined above admixed with a pharmaceutical carrier, diluent or excipient therefor. A preferred formulation is one suitable for oral administration.

Yet another embodiment of this invention is a method for treating bacterial infections in animals comprising administering an effective amount of an antibacterial compound of the above formula. In a preferred method of treatment, the benzothienylglycyl cephalosporin derivative is administered orally.

DETAILED DESCRIPTION OF THE INVENTION

In the above formulas defining the compounds provided by this invention, $R^1$ defines a 2-benzothienyl group of the formula

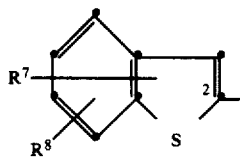

or a 2-(4,5,6,7-tetrahydrobenzothienyl) group of the formula

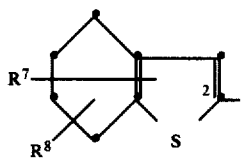

These benzothienyl and tetrahydrobenzothienyl groups are mono-substituted, for instance when one of $R^7$ or $R^8$ is hydrogen and one is other than hydrogen; or they can be di-substituted, for instance when $R^7$ and $R^8$ both are other than hydrogen. $R^7$ can be located at the 3-position of the bicyclic ring system, or at the 4, 5, 6 or 7 position. $R^7$ and $R^8$ are defined to include $C_1$-$C_4$ alkyl, $C_1$-$C_4$ alkoxy, halo, $C_1$-$C_4$ alkanoylamino and $C_1$-$C_4$ alkylsulfonylamino. The term "$C_1$-$C_4$ alkyl" carries its art-recognized meaning of straight and branched lower alkyl carbon chains such as methyl, ethyl, isopropyl, n-propyl, iso-butyl and tert.-butyl. Similarly, "$C_1$-$C_4$ alkoxy" refers to lower alkyl groups bonded to the benzothienyl or tetrahydrobenzothienyl bicyclic ring through an oxygen atom. Typical $C_1$-$C_4$ alkoxy groups include methoxy, ethoxy, n-propoxy, n-butoxy and isobutoxy. The term "halo" as used herein includes fluoro, chloro, bromo and iodo. Preferred halo groups include chloro and fluoro.

$R^7$ and $R^8$ also represent $C_1$-$C_4$ alkanoylamino and $C_1$-$C_4$ alkylsulfonylamino. Typical alkanoylamino groups include formylamino, acetylamino, and isobutyrylamino. Typical $C_1$-$C_4$ alkylsulfonylamino groups are methylsulfonylamino, ethylsulfonylamino and n-butylsulfonylamino.

When $R^7$ and $R^8$ are on adjacent carbon atoms, they can be taken together to form a methylenedioxy group, for example to form an $R^1$ substituent such as

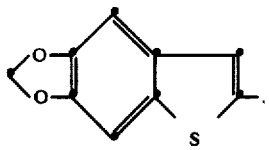

$R^2$ in the above formula defines a substituent on the glycyl nitrogen atom, and includes hydrogen and an amino protecting group. The term "amino protecting group" refers to any of the art-recognized substituents that can be attached to an amino nitrogen atom and which is readily removed when desired. Such protecting groups are often employed during preparation of the compounds of the invention, and serve to improve solubility in organic solvents and to decrease the likelihood of unwanted side reactions occurring as a result of the presence of a free amino group. While the compounds wherein $R^2$ is a protecting group are expected to have biological activity, it is contemplated that the most biologically desirable compounds will be those wherein $R^2$ is hydrogen. The compounds wherein $R^2$ is an amino protecting group are thus primarily useful as intermediates in the synthesis of the more preferred free amino compounds.

The precise nature of the amino protecting group is not critical to the invention, and any of the well known protecting groups can be employed. Typical amino protecting groups are described by J. W. Barton in "Protective Groups in Organic Chemistry," J. F. McOmie, Ed., Plenum Press, New York, N.Y., 1973 Chapter 2, and by Greene in "Protective Groups in Organic Synthesis," John Wiley and Sons, New York, N.Y., 1981, Chapter 7. Both of these references are incorporated herein by reference for their teaching of amine protecting groups.

The most common amino protecting groups to be employed include $C_1$-$C_{10}$ alkanoyl groups such as formyl, acetyl, dichloroacetyl, propionyl, hexanoyl 3,3-diethylhexanoyl, γ-chlorobutyryl, and the like; $C_1$-$C_{10}$ alkoxycarbonyl and $C_5$-$C_{15}$ aryloxycarbonyl groups such as tert.-butoxycarbonyl, benzyloxycarbonyl, allyloxycarbonyl, 4-nitrobenzyloxycarbonyl and cinnamoyloxycarbonyl; halo-$C_1$-$C_{10}$ alkoxycarbonyl such as 2,2,2-trichloroethoxycarbonyl; and $C_1$-$C_{15}$ arylalkyl and alkenyl groups such as benzyl, phenethyl, allyl, trityl, and the like. Other commonly used amino protecting groups are those in the form of enamines prepared with β-keto-esters such as methyl or ethyl acetoacetate.

$R^2$ in the above formula, in addition to representing hydrogen or an amino protecting group, also, when taken together with $R^3$, completes a ring system to provide compounds of the formula

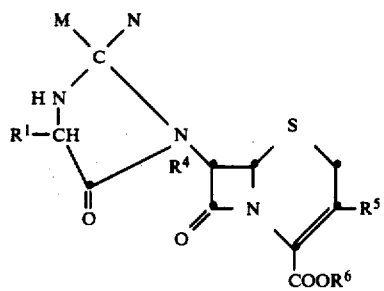

where $R^1$, $R^4$, $R^5$, $R^6$, M, and N are as defined above. Typical of these compounds are the acetonides, for example those wherein M and N both are methyl. Such compounds are particularly useful as long-acting antibacterial agents.

$R^6$ in the above formula is hydrogen; a salt forming group such as ammonium or an alkali metal cation, for example lithium, sodium or potassium; or a carboxy protecting group. The term "carboxy protecting group" refers to the art-recognized groups commonly employed to block or protect the carboxylic acid functionality of a cephalosporin molecule during chemical reactions involving other functional sites in the molecule, and which can be readily removed when desired by common hydrolytic or hydrogenolytic techniques. Typical carboxy protecting groups to be employed according to this invention include those described by E. Haslam in "Protective Groups in Organic Chemistry", supra, Chapter 5, and by Greene in "Protective Groups in Organic Synthesis," supra, Chapter 5, which are incorporated herein by reference. Examples of the commonly employed carboxy protecting groups include $C_1$–$C_{10}$ alkyl groups such as methyl, tert.-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri($C_1$–$C_3$ alkyl)silyl such as trimethylsilyl, β-p-toluenesulfonylethyl, β-p-nitrophenylthioethyl, 2,4,6-trimethylbenzyl, β-methylthioethyl, phthalimidomethyl, 2,4-dinitrophenylsulphenyl, 2-nitrobenzhydryl and related groups.

The benzothienylglycyl cephalosporin derivatives provided by this invention can be prepared by any of several methods. A preferred method comprises reacting a 7-aminocephalosporin nucleus with a benzothienylglycine derivative according to the following scheme:

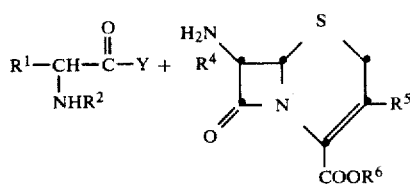

wherein $R^1$, $R^2$, $R^4$, $R^5$ and $R^6$ are as defined above, and Y is a leaving group such as hydroxy; halo, for instance chloro, bromo, or iodo; lower alkanoyloxy such as formyloxy, acetoxy or the like. Typical benzothienylglycine derivatives commonly employed in such direct coupling reactions include those of the formula

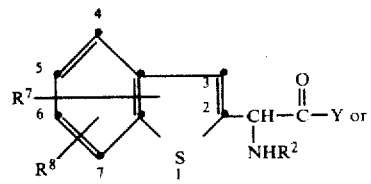

wherein:

| $R^7$ | $R^8$ | $R^2$ | Y |
|---|---|---|---|
| 3-Cl | H | chloroacetyl | OH |
| 3-OCH$_3$ | H | formyl | Cl |

-continued

| $R^7$ | $R^8$ | $R^2$ | Y |
|---|---|---|---|
| 4-OCH$_3$ | H | H | Cl (as a hydrochloride) |
| 5-CH$_3$ | H | formyl | OCHO |
| 5-Cl | H | tert.-butoxycarbonyl | OH |
| 6-OH | H | 4-chlorobutyryl | OH |
| 5-OCH$_3$ | H | acetyl | OH |
| 6-OCH$_3$ | 4-Cl | tert.-butoxycarbonyl | Cl |
| 3-OCH$_3$ | 5-Br | benzyl | Br |
| 7-OCH$_2$CH$_3$ | H | trimethylsilyl | OCHO |
| 4-OCH$_3$ | 5-OCH$_3$ | p-nitrobenzyl | OCOCH$_3$ |
| 3-Cl | 6-NO$_2$ | H | Br (hydrobromide) |
| 3-Br | 6-NH$_2$ | benzyloxycarbonyl | Br |
| 4-F | H | tert.-butoxycarbonyl | Cl |
| 7-Cl | H | H | Cl (hydrochloride) |
| 7-I | 4-acetylamino | 2,2,2-trichloroethoxycarbonyl | Cl |
| 3-CH$_3$ | H | —C=CHCOOCH$_3$<br>     \|<br>     CH$_3$ | Cl |
| 4-CH$_3$ | H | H | OH |
| 3-CH$_3$ | 5-CH$_2$CH$_3$ | formyl | Cl |
| 7-CH$_2$CH$_3$ | H | acetyl | OH |
| 5-CH$_2$CH$_2$CH$_3$ | 6-F | benzoyl | HCHO |
| H | 6-methylsulfonylamino | H | Cl (hydrochloride) |
| H | 5-Cl | allyloxycarbonyl | OCOCH$_3$. |

The benzothienylglycine derivatives thus described are either known commercially or are available by methods generally familiar to those skilled in the art of organic chemistry.

Like the benzothienylglycine starting materials, the cephalosporin nuclei required for the synthesis of the present compounds are readily available or can be prepared by methods well known in the art. For example, the 3-halo cephalosporin nuclei can be prepared by the methods taught in U.S. Pat. No. 3,925,372. 3-Methyl cephalosporins are available by ring expansion of penicillin sulfoxides and subsequent side chain cleavage. The 3-vinyl cephem nucleus is available by the method of U.S. Pat. No. 3,994,884.

Typical cephalosporin nuclei that will be employed in the synthesis of compounds of the present invention are illustrated below:

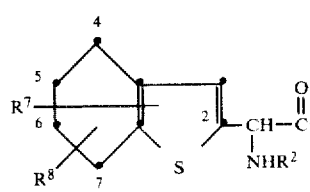

| $R^4$ | $R^5$ | $R^6$ |
|---|---|---|
| H | CH$_3$ | H |
| H | CH$_3$ | tert.-butyl |
| H | Cl | p-nitrobenzyl |
| CH$_3$O | H | methyl |
| CH$_3$S | CH$_3$ | H |
| H | —CH$_2$OCH$_3$ | 2,2,2-trichloroethyl |
| H | —CH=CH$_2$ | benzyl |

-continued

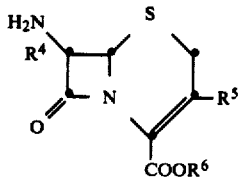

| R⁴ | R⁵ | R⁶ |
|---|---|---|
| H | OCH₃ | allyl |
| CH₃O | Br | trimethylsilyl |
| CH₃S | H | tert.-butyl |
| H | I | Na |

The coupling of a benzothienylglycine derivative with a 7-aminocephalosporin nucleus can be accomplished employing common techniques of acylation. For example, a benzothienylglycyl acylating agent, wherein Y in the above formula is a leaving group such as halo, especially chloro or bromo, or alkanoyloxy such as formyloxy or acetoxy, can be reacted with a cephalosporin nucleus employing standard acylation conditions. During such acylation reaction, it generally is preferred that $R^2$ in the above formula be an amino protecting group and that $R^6$ be a carboxy protecting group. These protecting groups serve to minimize unwanted side reactions and to increase solubility characteristics of the respective reactants.

The acylation reaction generally is accomplished by combining approximately equimolar quantities of a benzothienylglycyl acylating agent (i.e. an acid halide or mixed acid anhydride) with the 7-aminocephalosporin nucleus. The acylation reaction normally is carried out in a mutual solvent such as benzene, chloroform, dichloromethane, toluene, N,N-dimethylformamide, acetonitrile, or the like, and routinely is substantially complete after about 1 to about 12 hours when conducted at a temperature of about −20° to about 60° C. About an equimolar quantity of a base such as pyridine, triethylamine, aniline, sodium carbonate or the like, can be employed in the reaction if desired to act as an acid scavenger. The product may be isolated from the reaction mixture by simply removing the reaction solvent, for instance by evaporation under reduced pressure, and further purification can be accomplished if needed employing routine techniques such as chromatography, crystallization, solvent extraction, and related methods.

An alternative and preferred method for coupling a benzothienylglycine derivative to a 7-aminocephalosporin nucleus to produce compounds of the invention employs a coupling reagent such as those routinely used in the synthesis of peptides. Typical coupling reagents that can be employed include carbodiimides such as N,N'-diethylcarbodiimide, N,N-diisopropylcarbodiimide, and N,N-dicyclohexylcarbodiimide (DCC); carbonyl coupling reagents such as carbonyldiimidazole; isoxazolinium salts such as N-ethyl-5'-phenylisoxazolinium-3'-sulfonate; and quinoline compounds such as N-ethoxycarbonyl-2-ethoxy-1,2-dihydroquinoline (EEDQ).

The coupling of a 7-aminocephalosporin nucleus with a benzothienylglycine derivative employing a peptide coupling reagent generally is accomplished by combining approximately equimolar quantities of a 7-aminoceph-3-em-4-carboxylic acid, a benzothienylglycine, and a peptide coupling reagent according to the following scheme;

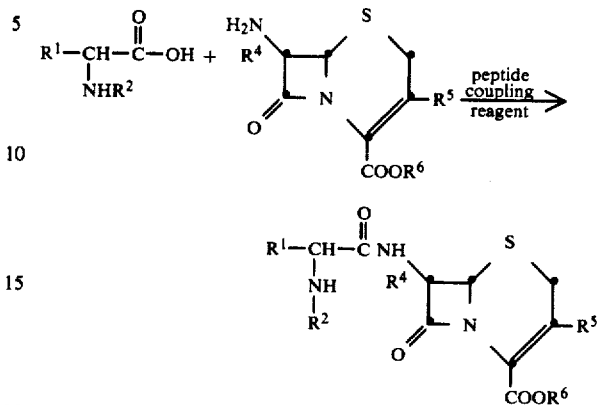

wherein $R^1$, $R^2$, $R^4$, $R^5$ and $R^6$ are as defined above. Preferably $R^2$ is an amino protecting group and $R^6$ is hydrogen or a carboxy protecting group during such coupling reactions. Any such protecting groups can be subsequently removed by standard methods to give the active antibiotic of the invention.

The coupling reaction normally is conducted in a mutual solvent such as dichloromethane, acetone, water, acetonitrile, N,N-dimethylformamide, chloroform, or the like, and routinely is substantially complete when carried out for about ten to about ninety minutes at a temperature of about −20° to about 60° C. Longer reaction periods are not detrimental to the product and can be employed if desired. The product, a benzothienylglycyl cephalosporin derivative of the invention, is readily isolated by simply removing the reaction solvent, for instance by evaporation under reduced pressure. The product can be purified if needed by standard methods such as acid-base extraction, chromatography, salt formation or the like.

Yet another alternative method for preparing compounds of the invention comprises chemically modifying a position other than the side chain of a benzothienylglycyl cephalosporin. For example, a 3-exomethylene cephalosporin nucleus can be acylated with a benzothienylglycyl derivative to form a benzothienylglycyl 3-exomethylene cephalosporin. The latter compound can be converted by known methods to compounds of the invention. For instance, ozonolysis of a benzothienylglycyl 3-exomethylene cephalosporin affords a 3-hydroxy compound. Halogenation of a 3-hydroxy compound affords the 3-halo benzothienylglycyl cephalosporins of the invention, while reaction with a base and a methylating agent affords the 3-methoxy compounds of the invention.

Still another method for preparing compounds of the invention employs a benzothienyl oxime derivative of the formula

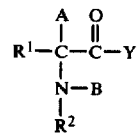

wherein $R^1$ and Y have the above-defined meanings, A and B are taken together to form a bond, and $R^2$ is hydroxy or methoxy. When $R^2$ is hydroxy, it generally is protected with trimethylsilyl, p-nitrobenzyl, or similar hydroxy protecting group during the coupling reaction. Such benzothienyl oxime derivatives can be coupled to a cephalosporin nucleus by any of the methods described above to provide a compound of the formula

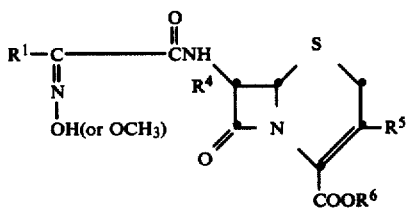

wherein $R^1$, $R^4$, $R^5$, and $R^6$ are as define above. These compounds are useful as intermediates since they are readily reduced by normal methods to give the preferred benzothienylglycyl compounds of the invention. Additionally, the oximes of the above formula wherein $R^6$ is hydrogen or a salt forming group are useful antibiotics.

Compounds of the invention that bear a nitro group on the benzothienylglycyl or the tetrahydrobenzothienylglycyl side chain can be modified to provide other compounds of the invention. For example, the nitro substituent can be reduced by routine reduction or hydrogenation procedures to give the corresponding amino substituted benzothienylglycyl cephalosporin derivative, which if desired can be acylated by reaction with a $C_1$-$C_4$ alkanoyl halide or anhydride or a $C_1$-$C_4$ alkylsulfonyl halide to provide the corresponding alkanoylamino or alkylsulfonylamino benzothienylglycylamido cephalosporin of the invention.

Similarly, compounds of the invention wherein $R^2$ and $R^3$ are taken together to form the group

are prepared by reacting a ketone of the formula

with a compound of the invention wherein $R^2$ and $R^3$ both are hydrogen, generally in the presence of a catalytic amount of an acid such as methanesulfonic acid or the like. The cyclic compounds thus produced, for instance the preferred acetonides wherein M and N both are methyl, are particularly useful as oral antibiotics since they are effective over prolonged periods of time.

Other compounds of the invention that are expected to be particularly long acting antibiotics are those wherein $R^2$ is an alkanoyl amino protecting group such as formyl or acetyl. Such compounds are conveniently prepared by simply reacting a benzothienylglycylamido cephalosporin, wherein $R^2$ is hydrogen, with a $C_1$-$C_{10}$ alkanoyl acylating agent, for instance formyl chloride or acetic anhydride. These N-acylated products are expected to act not only as antibiotics in themselves, but also as pro-drugs in that they will be hydrolyzed in an animal system to the parent benzothienylglycyl derivative.

It should be noted that since the benzothienylglycyl side chains of the cephalosporins of this invention contain one asymmetric carbon atom, for example when A is hydrogen, the compounds of the invention can exist in the form of optical isomers, namely the D and the L isomers. The compounds of the invention can be employed as a DL-mixture to treat bacterial infections in animals, or if desired the optical isomers can be separated and employed individually. While both isomers are effective antibacterial agents, one isomer appears to be more potent than the other and is designated herein as the D-isomer, and accordingly is a preferred embodiment of the invention.

Separation or racemization of the optical isomers can be accomplished by routine methods carried out on the cephalosporin product of the invention or on the benzothienylglycine side chain that is employed as a starting material. Separation of optical isomers generally will be accomplished by high performance chromatography, enzymatic resolution, or chemical crystallization or racemization. A particularly preferred method for obtaining a D-(2-benzothienyl)glycine comprises reacting the D,L-mixture with benzaldehyde and optically active tartaric acid according to the method of U.S. Pat. No. 3,976,680. Another preferred method of resolution employs an N-acyl L-amino acid amidohydrolase enzyme, for instance according to the method described in U.S. Pat. No. 3,386,888.

As noted above, preferred compounds of the invention are those wherein $R^2$ in the above formula is hydrogen. Such compounds, being primary amines, are basic in nature and readily form pharmaceutically acceptable salts by reaction with acids. Typical acids commonly employed to form salts include inorganic acids such as hydrogen chloride, hydrogen bromide, sulfuric acid, phosphoric acid; as well as organic acids such as acetic acid, trifluoroacetic acid, succinic acid, methanesulfonic acid, oxalic acid, para-toluenesulfonic acid, and the like. The compounds of the invention wherein both $R^2$ and $R^6$ are hydrogen readily form an internal acid addition salt, namely a zwitterion.

Examples of typical classes of benzothienylglycyl cephalosporins, as well as specific compounds provided by this invention, include those listed below:

Preferred Compounds of the formula

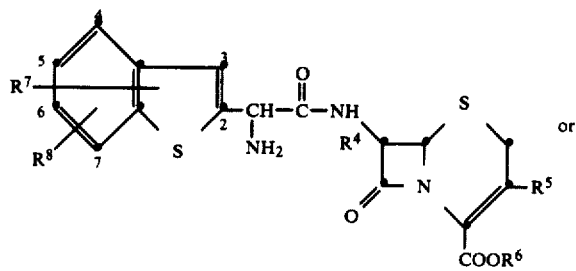

or

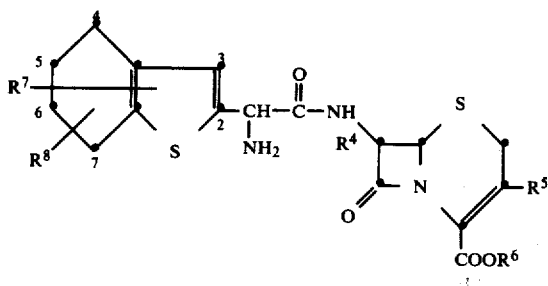

| R⁷ | R⁸ | R⁴ | R⁵ | R⁶ |
|---|---|---|---|---|
| 4-Cl | H | H | CH₃ | H |
| 5-I | H | H | Cl | H |
| 6-OCH₃ | H | H | CH=CH₂ | H |
| 7-CH₃ | 4-Cl | H | H | Na⁺ |
| 3-OH | H | CH₃O— | CH₂OCH₃ | H |
| 4-Br | 7-CH₃ | H | OCH₃ | H |
| 3-CH₃ | 6-OCH₂CH₃ | CH₃S— | Br | NH₄⁺ |
| 5-F | 6-F | H | CH₃ | H |
| H | 6-NO₂ | H | CH₃ | K⁺ |
| H | 6-NH₂ | H | CH₃ | H |
| H | 6-NHCOCH₃ | CH₃O— | F | H |
| 3-Cl | 6-NHSO₂CH₂CH₃ | H | CH=CH₂ | H |
| 5-OCH₂CH(CH₃)₂ | H | H | H | tert-butyl |
| 6-OH | 7-CH₃ | CH₃S— | CH₂OCH₃ | p-nitrobenzyl |
| 7-Cl | H | H | CH₃ | CH₂CH=CH₂ |
| 3-Br | H | H | Cl | CH₂CCl₃ (hydrochloride) |
| 6-Cl | H | H | OCH₃ | trimethylsilyl |

Compounds of the formula

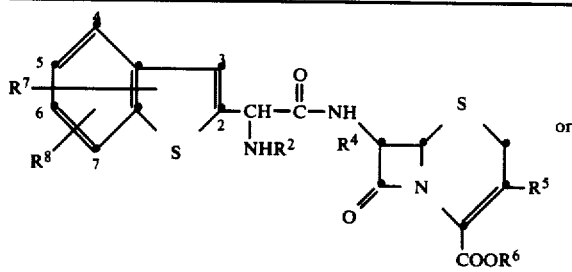

or

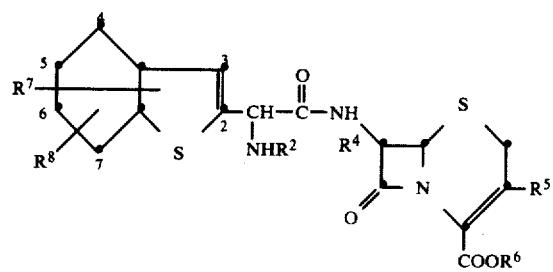

-continued

Compounds of the formula

| R⁷ | R⁸ | R² | R⁴ | R⁵ | R⁶ |
|---|---|---|---|---|---|
| 4-Cl | H | COOtert.butyl | H | $CH_3$ | H |
| 5-$OCH_3$ | H | $COOCH_2CH=CH_2$ | H | Cl | H |
| H | 6-$OCH_3$ | $COCH_3$ | $CH_3O$ | H | H |
| 3-Cl | 6-$OCH_3$ | $COOCH_2CCl_3$ | H | $OCH_3$ | $CH_2CCl_3$ |
| 4-$CH_3$ | H | $CH_2\phi$ | H | $CH_2OCH_3$ | p-nitrobenzyl |
| 5-Br | 6-Br | $C(\phi)_3$ | $CH_3S$ | Br | $CH_3$ |
| H | 6-OH | $CH\phi$ | H | $CH=CH_2$ | $CH_2OCOCH_3$ |
| 6,7-methylene-dioxy | | $Si(CH_3)_3$ | H | I | $Si(CH_3)_3$ |
| 3-Et | H | $COOCH_2$-⟨C₆H₄⟩-$NO_2$ | H | $CH_3$ | $CH_2$-⟨C₆H₄⟩-$NO_2$ |

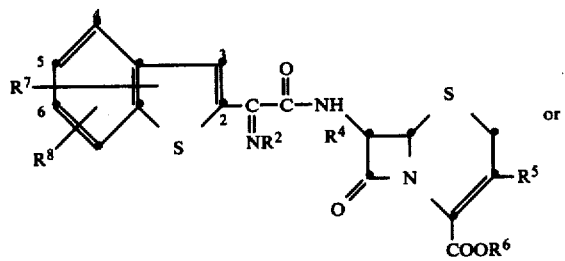

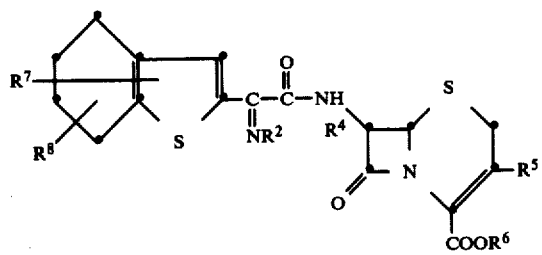

| R⁷ | R⁸ | R² | R⁴ | R⁵ | R⁶ |
|---|---|---|---|---|---|
| 4-Cl | H | OH | H | $CH_3$ | H |
| 5-$OCH_3$ | H | $OCH_3$ | H | Cl | H |
| 6-$NO_2$ | H | OH | $CH_3O$ | $CH_2OCH_3$ | H |
| 7-$CH_3$ | H | $OCH_3$ | H | H | tert.-butyl |
| H | 6-F | $OCH_3$ | H | $CH=CH_2$ | p-nitrobenzyl |
| 3-Cl | 7-$OCH_3$ | OH | $CH_3S$ | F | $CH_2CCl_3$ |
| 3-Br | H | $OCH_3$ | H | $CH_3$ | $Na^+$ |
| 4-Cl | 5-Cl | $OCH_3$ | H | $CH_3$ | $CH_3$ |
| 5-$NH_2$ | H | OH | H | Cl | $CH_2CH=CH_2$ |
| 5-$NHCOCH_3$ | H | $OCH_3$ | H | $OCH_3$ | $CH(Cl)_2$ |

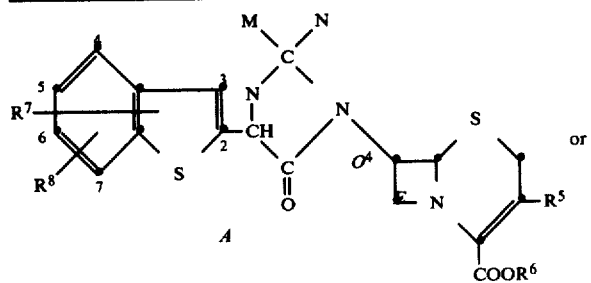

-continued

Compounds of the formula

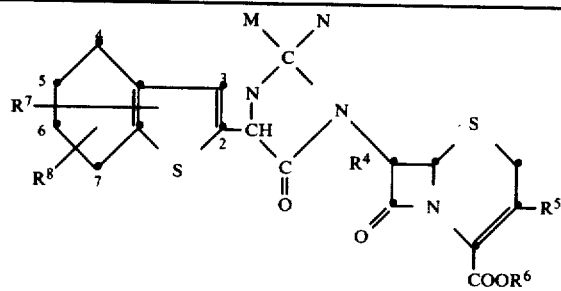

| $R^7$ | $R^8$ | M | N | $R^4$ | $R^5$ | 6 |
| --- | --- | --- | --- | --- | --- | --- |
| 4-$CH_3$ | H | $CH_3$ | $CH_3$ | H | $CH_3$ | H |
| 4-$OCH_3$ | 5-F | $CH_3$ | $CH_3$ | H | Cl | $Na^+$ |
| H | 6-$OCH_3$ | $CH_3$ | $CH_3$ | $CH_3O$ | $OCH_3$ | tert.-butyl |
| 3-Cl | H | $CH_3$ | $CH_3$ | $CH_3S$ | H | H |
| 3-$OCH_3$ | 5-$CH_3$ | $CH_2CH_3$ | $CH_3$ | H | $CH_3$ | $CH(\phi)_2$ |
| 5-F | 6-F | $CH_3$ | $CH_3$ | H | $CH=CH_2$ | $CH_2CH=CH_2$ |

The synthesis of the compounds provided by this invention is further illustrated by the following preparations and working examples. The examples are illustrative only and are not intended to limit the invention in any respect.

Preparation 1

α-Methoxyimino-α-(5-chloro-2-benzothienyl)acetic acid

Methylthio α-oxo-α-(5-chloro-2-benzothienyl)acetate was prepared by reacting 26.8 g of methyl (5-chloro-2-benzothienyl)formate with 21.4 g of methyl methylthiomethyl sulfoxide in 500 ml of N,N-dimethylformamide to give 1-oxo-1-(5-chloro-2-benzothienyl)-2-methylthio-2-methylsulfinylethane, which was then reacted with sodium para periodate in acetic anhydride and formic acid.

A solution of 2.6 g of methylthio α-oxo-α-(5-chloro-2-benzothienyl)acetate in 180 ml of methanol containing 840 mg of hydroxylamine hydrochloride and 10 ml of 1N sodium hydroxide was stirred at 25° C. for sixteen hours. The reaction solvent was removed by evaporation under reduced pressure to give an oil. The oil was dissolved in 100 ml of ethyl acetate and 100 ml of water, and the mixture was made alkaline to pH 10.4 by addition of 1N sodium hydroxide. The aqueous layer was separated, washed with fresh ethyl acetate, and then made acidic to pH 2 by addition of 1N hydrochloric acid. The aqueous acid mixture was extracted with fresh ethyl acetate, which was then washed with water, dried and the solvent was removed to provide 2.5 g of α-methoxyimino-α-(5-chloro-2-benzothienyl)acetic acid.

Analysis calculated for $C_{11}H_8NO_3SCl$: Theory: C, 48.99; H, 2.99; N, 5.19. Found: C, 49.24; H, 2.70; N, 4.91.

NMR(DCDl₃) δ 4.10 and 4.22 (two singlets, 3H); δ 7.20–8.19 (m, 4H); δ 10.15 (broad s, 1H).

The following benzothienyl acetic acid derivatives can be prepared by the general method described above.

α-Methoxyimino-α-(3-methoxy-2-benzothienyl)acetic acid;
α-Methoxyimino-α-(6-methoxy-2-benzothienyl)acetic acid;
α-Methoxyimino-α-(3-methyl-7-fluoro-2-benzothienyl)acetic acid;
α-Methoxyimino-α-(4-nitro-2-benzothienyl)acetic acid;
α-Methoxyimino-α-(4-chloro-2-benzothienyl)acetic acid.

Preparation 2

Ethyl α-oxo-α-(4,5,6,7-tetrahydro-2-benzothienyl)acetate 4-(2-Thienyl)butyric acid was reacted with thionyl chloride and stannic chloride to provide 5-oxo-4,5,6,7-tetrahydrobenzothiophene, which upon reaction with hydrazine and sodium hyroxide gave 4,5,6,7-tetrahydrobenzothiophene. A solution of 13.3 g of 4,5,6,7-tetrahydrobenzothiophene in 150 ml of dichloromethane was added dropwise to a stirred suspension of 13.1 g of ethyl oxalyl chloride and 14.0 g of aluminum chloride in 200 ml of dichloromethane. The reaction mixture was stirred for twelve hours at 25° C. following the addition. The reaction mixture was poured into 500 g of ice and then the organic layer was separated, dried, and the solvent was removed by evaporation to give 19.2 g of ethyl α-oxo-α-(4,5,6,7-tetrahydro-2-benzothienyl)acetate.

NMR(CDCl₃): δ 1.44 (triplet, 3H); δ 1.88 (m, 4H); δ 2.76 (m, 4H); δ 4.40 (q, 2H); δ 7.75 (s, 1H).

The following compounds are prepared by the general procedure described above:

Ethyl α-oxo-α-(3-methoxy-4,5,6,7-tetrahydro-2-benzothienyl)acetate;
Ethyl α-oxo-α-(5-chloro-4,5,6,7-tetrahydro-2-benzothienyl)acetate;
Methyl α-oxo-α-(7-nitro-4,5,6,7-tetrahydro-2-benzothienyl)acetate; and
Ethyl α-oxo-α-(3-bromo-6-methyl-4,5,6,7-tetrahydro-2-benzothienyl)acetate.

Preparation 3

D,L Ethyl-α-amino-α-(4,5,6,7-tetrahydro-2-benzothienyl)acetate

A solution of 14.0 g of ethyl α-oxo-α-(4,5,6,7-tetrahydro-2-benzothienyl)acetate in 300 ml of ethanol containing 5.31 g of sodium acetate and 6.50 g of hydroxylamine hydrochloride was heated at reflux for three hours.

The reaction mixture was cooled and the solvent was removed by evaporation under reduced pressure to provide 14.7 g of ethyl α-hydroxyimino-α-(4,5,6,7-tetrahydro-2-benzothienyl)acetate.

To a cold (5° C.) stirred solution of the oxime from above in 120 ml of methanol containing 75 ml of 90% formic acid and 60 ml of water were added portionwise over forty minutes 7.58 g of zinc metal dust. Following complete addition, the reaction mixture was stored at 0° C. for twelve hours. After warming the mixture to about 25° C., it was filtered and the filtrate was concentrated to dryness to give an oil. The oil was dissolved in 100 ml of 1N hydrochloric acid and the solution was washed with 50 ml of ethyl acetate. The aqueous layer was made alkaline to pH 8 by addition of 1N sodium hydroxide, and the product was extracted into ethyl acetate, which was dried and concentrated to afford 12.74 g of D,L-ethyl α-amino-α-(4,5,6,7-tetrahydro-2-benzothienyl)acetate.

NMR(CDCl$_3$): δ 1.27 (triplet, 3H); δ 2.79 (m, 4H); δ 2.50 (m, 6H); δ 4.20 (q, 2H); δ 4.75 (s, 1H); δ 6.64 (s, 1H).

Preparation 4

D,L-N-tert.-Butoxycarbonyl (4,5,6,7-tetrahydro-2-benzothienyl)glycine

A solution of 2.6 g of D,L-ethyl α-amino-α-(4,5,6,7-tetrahydro-2-benzothienyl)acetate in 30 ml of ethanol and 100 ml of 1N sodium hydroxide was stirred at 25° C. for two hours. The reaction mixture was diluted by addition of 50 ml of tetrahydrofuran, and then 4.5 ml of di-tert.butyl dicarbonate were added and stirring was continued for an additional twelve hours. The organic solvents were next removed by evaporation and the aqueous mixture was washed with 100 ml of 1:1 ethyl acetate-diethyl ether. The aqueous layer was separated and made acidic to pH 2.3 by addition of 1N hydrochloric acid. The aqueous acid solution was extracted with ethyl acetate, and the organic layer was washed with water, dried and concentrated to dryness to afford 2.50 g (73% yield) of D,L-N-tert.-butoxycarbonyl(4,5,6,7-tetrahydro-2-benzothienyl)glycine. NMR(CDCl$_3$): δ 1.42 (s, 9H); δ 1.75 (m, 4H); δ 5.46 (broad, 2H); δ 6.74 (s, 1H).

By following the general procedures of Preparations 3 and 4, the following 2-benzothienylglycine derivatives can be prepared:

N-chloroacetyl(4-chloro-4,5,6,7-tetrahydro-2-benzothienyl)glycine;

N-2,2,2-trichloroethoxycarbonyl(6-ethoxy-4,5,6,7-tetrahydro-2-benzothienyl)glycine;

N-allyloxycarbonyl(3-fluoro-4,5,6,7-tetrahydro-2-benzothienyl)glycine; and

N-para-nitrobenzyl(3,4-difluoro-4,5,6,7-tetrahydro-2-benzothienyl)glycine.

EXAMPLE 1

7-[α-Methoxyimino-α-(5-chloro-2-benzothienyl)acetamido]-3-methyl-3-cephem-4-carboxylic acid A solution of 255 mg (1 mM) of α-methoxyimino-α-(5-chloro-2-benzothienyl)acetic acid (from Preparation 1) in 10 ml of oxalyl chloride containing three drops of N,N-dimethylformamide was stirred at 0° C. for two hours. The excess oxalyl chloride was removed by evaporation under reduced pressure and by azeotroping with three 50 ml portions of acetonitrile. The residue was disssolved in 15 ml of acetonitrile and added in one portion to a cold (0° C.) stirred solution of 428 mg of 7-amino-3-methyl-3-cephem-4-carboxylic acid in 50 ml of acetonitrile containing 2.5 ml of bis(trimethylsilyl)trifluoroacetamide. The reaction mixture was stirred for three hours at 0° C. and then stored at −5° C. for twelve hours. The reaction mixture was warmed to 25° C. and then diluted by addition of 5 ml of dilute ammonium hydroxide and filtered. The filtrate was concentrated to dryness to give a gum which was then dissolved in 20 ml of aqueous sodium bicarbonate and 20 ml of ethyl acetate. The mixture was acidified to pH 2 by addition of dilute hydrochloric acid. The organic layer was separated, dried and the solvent was removed by evaporation to give 400 mg of 7-[α-methoxyimino-α-(5-chloro-2-benzothienyl)acetamido]-3-methyl-3-cephem-4-carboxylic acid.

NMR(CDCl$_3$): δ 2.20 (s, 3H); δ 3.50 (m, 2H); δ 4.05 (s, 3H); δ 4.22 (s, 1H); δ 5.10 (m, 1H); δ 5.90 (m, 1H); δ 6.2–6.7 (broad, 1H); δ 7.22–8.6 (m, 4H).

EXAMPLE 2

D-7-(5-Chloro-2-benzothienyl)glycylamido-3-methyl-3-cephem-4-carboxylic acid

To a cold (0° C.) stirred solution of 400 mg of 7-[α-methoxyimino-α-(5-chloro-2-benzothienyl)acetamido]-3-cephem-4-carboxylic acid (from Example 1) in 8 ml of methanol containing 8 ml of 90% formic acid and 5 ml of water were added portion-wise over twenty-five minutes 230 mg of zinc dust. The reaction mixture was stirred for two and one-half hours at 0° C. following complete addition. The reaction mixture was filtered and the solvent was removed from the filtrate by evaporation under reduced pressure to provide 462 mg of D,L-7-(5-chloro-2-benzothienyl)glycylamido-3-methyl-3-cephem-4-carboxylic acid. High pressure liquid chromatography effected separation of isomers to provide D-7-(5-chloro-2-benzothienyl)glycylamido-3-methyl-3-cephem-4-carboxylic acid.

NMR(TFA$_{d1}$): δ 2.32 (s, 3H); δ 4.10 (s, 2H); δ 5.22 (d, 1H); δ 5.8.1 (d, 1H); δ 6.00 (s, 1H); δ 7.50–7.88 (m, 4H).

EXAMPLE 3 p-Nitrobenzyl 7-[N-tert.-butoxycarbonyl(4,5,6,7-tetrahydro-2-benzothienyl)glycylamido]-3-methyl-3-cephem-4-carboxylate A solution of 622 mg of N-tert.-butoxycarbonyl(4,5,6,7-tetrahydro-2-benzothienyl)glycine (from Preparation 4) in 50 ml of acetonitrile containing 494 mg of N-ethoxycarbonyl-2-ethoxy-1,2-dihydroquinoline was stirred for five minutes and then added in one portion to a cold (0° C.) stirred solution of 770 mg of p-nitrobenzyl 7-amino-3-methyl-3-cephem-4-carboxylate in 250 ml of acetonitrile. The reaction mixture was stirred at 0° C. for thirty minutes and then was warmed to 25° C. and stirred for an additional twelve hours. The reaction mixture was concentrated to an oil by evaporation of the solvent, and the oil was dissolved in 100 ml of ethyl acetate. The solution was washed once with 1N hydrochloric acid, then with aqueous sodium bicarbonate, and finally with brine. After drying the solution, the solvent was removed by evaporation under reduced pressure to give 1.23 g (59% yield) of para-nitrobenzyl 7-[N-tert.-butoxycarbonyl-(4,5,6,7-tetrahydro-2-benzothienyl)glycylamido]-3-methyl-3-cephem-4-carboxylate.

NMR(CDCl$_3$): δ 1.42 (s, 9H); δ 1.79 (m, 4H); δ 2.64 (m, 4H); δ 3.32 (m, 2H); δ 4.99 (m, 1H); δ 5.31 (s, 2H);

δ 5.41 (s, 2H); δ 5.75 (m, 1H); δ 6.72 (s, 1H); δ 6.99 (m, 1H); δ 7.55 (d, 2H); δ 8.20 (d, 2H).

EXAMPLE 4

7-[N-tert.-Butoxycarbonyl-(4,5,6,7-tetrahydro-2-benzothienyl)glycylamido]-3-methyl-3-cephem-4-carboxylic acid A suspension of 1.8 g of 5% palladium on carbon in 10 ml of ethanol and 30 ml of methanol was stirred at 25° C. for thirty minutes under hydrogen at 60 psi. A solution of 1.23 g of para-nitrobenzyl 7-[N-tert.-butoxycarbonyl-(4,5,6,7-tetrahydro-2-benzothienyl)-glycylamido]-3-methyl-3-cephem-4-carboxylate (from Example 3) in 60 ml of tetrahydrofuran was added in one portion to the reaction mixture and stirring was continued under hydrogen at 50 psi for fifty minutes. The reaction mixture was filtered and the filter cake was washed with ethyl acetate. The filtrate was then added to 50 ml of water and the mixture was made alkaline to pH 7.8. The aqueous layer was separated, made acidic to pH 2.2 by addition of 1N hydrochloric acid, and then extracted several times with ethyl acetate. The organic extracts were combined, dried, and concentrated to dryness to give 650 mg of D,L-7-[N-tert.-butoxycarbonyl-(4,5,6,7-tetrahydro-2-benzothienyl)glycylamido]-3-methyl-3-cephem-4-carboxylic acid.

NMR(CDCl$_3$): δ 1.42 (s, 9H); δ 1.80 (m, 4H); δ 2.18 (s, 3H); δ 2.60 (m, 4H); δ 3.29 (q, 2H); δ 5.00 (m, 1H); δ 5.4–5.9 (m, 3H); δ 6.72 (two s, 1H); δ 8.65 (broad, 2H).

EXAMPLE 5

7-[(4,5,6,7-Tetrahydro-2-benzothienyl)glycylamido]-3-methyl-3-cephem-4-carboxylic acid A solution of 650 mg of D,L-7-[N-tert.-butoxycarbonyl-(4,5,6,7-tetrahydro-2-benzothienyl)glycylamido]-3-methyl-3-cephem-4-carboxylic acid (from Example 4) in 8 ml of trifluoroacetic acid stood at room temperature for five minutes. The reaction mixture was added to 10 ml of water and the pH was adjusted to 7 by addition of dilute ammonium hydroxide. The neutral reaction mixture was filtered and the filtrate was concentrated in volume and then chromatographed over high pressure liquid chromatography, eluting with a mixture of 15% v/v acetonitrile, 1% ammonium acetate and 84% water to give the L-isomer and D-7-[(4,5,6,7-tetrahydro-2-benzothienyl)glycylamido]-3-methyl-3-cephem-4-carboxylic acid.

NMR(DMSO$_{d6}$): δ 2.0 (s, 3H); δ 3.42 (q, 2H); δ 4.7 (s, 1H); δ 5.03 (d, 1H); δ 5.63 (d, 1H); δ 6.67 (s, 1H).

EXAMPLE 6

7-[α-methoxyimino-α-(4-chloro-2-benzothienyl)acetamido]-3-methyl-3-cephem-4-carboxylic acid A solution of 539 mg (2 mM) of α-methoxy-α-(4-chloro-2-benzothienyl)acetic acid in 10 ml of benzene containing 0.72 ml (8 mM) of oxalyl chloride and two drops of N,N-dimethylformamide was stirred at 25° C. for thirty minutes. The solvent was then removed by evaporation to leave an oil, which was then purged three times with fresh benzene. The oil was next dissolved in 10 ml of acetone and added dropwise to a cold (0° C.) stirred solution of 428 mg (2 mM) of 7-amino-3-methyl-3-cephem-4-carboxylic acid in 20 ml of water and 10 ml of acetone containing 420 mg (5 mM) of sodium bicarbonate. The reaction mixture was stirred at 0° C. for thirty minutes following the addition, and then for three hours at room temperature. The reaction mixture was concentrated to a volume of about 20 ml and then diluted with 50 ml of ethyl acetate, and the pH was adjusted to 2.4 by addition of 1N hydrochloric acid. The organic layer was separated and the aqueous layer was extracted with fresh ethyl acetate. The organic extracts were combined, washed with water, dried, and the solvent was removed by evaporation to give 760 mg (81% yield) of 7-[α-methoxyimino-α-(4-chloro-2-benzothienyl)acetamido]-3-methyl-3-cephem-4-carboxylic acid.

NMR(CDCl$_3$): δ 2.19 (s, 3H); δ 3.39 (q, 2H); δ 4.07 and 4.23 (two singlets, 3H); δ 5.02–5.14 (m, 1H); δ 5.8–6.0 (m, 1H); δ 7.1–7.8 (m, 5H).

EXAMPLE 7

7-(4-Chloro-2-benzothienyl)glycylamido-3-methyl-3-cephem-4-carboxylic acid

To a stirred solution of 750 mg (1.6 mM) of 7-[α-methoxyimino-(4-chloro-2-benzothienyl)acetamido]-3-methyl-3-cephem-4-carboxylic acid (from Example 6) in 8 ml of methanol were added 8 ml of 98% formic acid and 5 ml of water. The solution was cooled to about 5° C., and then 386 mg (5.9 mM) of zinc metal dust were added portion wise over twenty minutes. The reaction mixture was stirred for three hours and then filtered through hyflow filter aid. The filtrate was concentrated to an oil which was dissolved in ethyl acetate and diethyl ether. A white precipitate was collected by filtration and dried at 40° C. in vacuum to give 984 mg of DL-7-(4-chloro-2-benzothienylglycylamido)-3-methyl-3-cephem-4-carboxylic acid.

The product thus formed was suspended in 30 ml of 5% (wt/v) aqueous sodium bicarbonate and 25 ml of water. The pH was adjusted to 8.5 by addition of 1N sodium hydroxide. High performance liquid chromatography over a C$_{18}$ reverse phase silica support, eluting with 2% acetic acid and a gradient of 10 to 20% (v/v) acetonitrile-water. The appropriate fractions were collected, concentrated and lyophilized to give:

Example 7A: 102 mg of D-7-(4-chloro-2-benzothienylglycylamido)-3-methyl-3-cephem-4-carboxylic acid;

Example 7B: 123 mg of L-7-(4-chloro-2-benzothienylglycylamido)-3-methyl-3-cephem-4-carboxylic acid;

NMR(DMSO$_{d6}$): δ 2.1 (s, 3H); δ 3.5 (q, 2H); δ 4.9 (s, 1H); δ 5.1 (d, 1H); δ 5.6 (d, 1H); δ 7.6 (m, 4H).

EXAMPLE 8

7-[α-Methoxyimino-α-(3-methoxy-2-benzothienyl)acetamido]-3-methyl-3-cephem-4-carboxylic acid Oxalyl chloride (0.72 ml, 8 mM) were reacted with 530 mg (2 mM) of α-methoxyimino-α-(3-methoxy-2-benzothienyl)acetic acid according to the method of Example 6 to give α-methoxyimino-α-(3-methoxy-2-benzothienyl)acetyl chloride. The acid chloride was dissolved in 20 ml of acetone and added dropwise to a cold (0° C.) stirred solution of 428 mg (2 mM) of 7-amino-3-methyl-3-cephem-4-carboxylic acid in 20 ml of acetone and 20 ml of water containing 420 mg (5 mM) of sodium bicarbonate. The reaction mixture was stirred for thirty minutes at 0° C. and then was warmed to 25° C. and stirred for an additional three hours. The reaction mixture was concentrated to a volume of about 20 ml and then was washed with ethyl acetate. The aqueous layer was layered with fresh ethyl acetate and the slurry was diluted with 1N hydrochloric acid to pH 2.4. The organic layer was separated, washed with water, dried, and the solvent was removed by evaporation to give 670 mg (72% yield) of 7-[α-methoxyimino-α-(3-methoxy-2-benzothienyl)acetamido]-3-methyl-3-cephem-4-carboxylic acid.

NMR(CDCl$_3$): δ 2.19 and 2.20 (two singlets, 3H); δ 3.4 (q, 2H); δ 3.98 and 4.01 (two singlets, 3H); δ 5.08 (d, 1H); δ 5.8–6.2 (m, 1H); δ 6.8–8.04 (m, 6H).

EXAMPLE 9

7-(3-Methoxy-2-benzothienyl)glycylamido-3-methyl-3-cephem-4-carboxylic acid

To a cold stirred solution of 660 mg of 7-[α-methoxyimino-α-(3-methoxy-2-benzothienyl)acetamido]-3-methyl-3-cephem-4-carboxylic acid (from Example 8) in 7 ml of methanol, 7 ml of formic acid and 3 ml of water were added portion wise over twenty minutes 344 mg (5.26 mM) of zinc metal dust. The reaction mixture was stirred at 0° C. for three hours and then filtered. The filtrate was concentrated to dryness to provide 1.1 g of a white powder. The powder was dissolved in 5.5 ml of 5% (wt/v) aqueous sodium bicarbonate and 15 ml of acetonitrile. The solution was filtered and the filtrate was chromatographed by high performance liquid chromatography over a C$_{18}$ reverse phase silica gel column eluting with 2% acetic acid and a gradient of 10 to 15% (v/v) acetonitrile/water. The appropriate fractions were combined, concentrated and lyophilized to yield:

Example 9A: 146 mg of D-7-(3-methoxy-2-benzothienylglycylamido)-3-methyl-3-cephem-4-carboxylic acid;

NMR(DMSO$_{d6}$): δ 2.0 (s, 3H); δ 3.4 (q, 2H); δ 4.0 (s, 3H); δ 5.1 (m, 2H); δ 5.6 (d, 1H); δ 7.6 (m, 4H).

Example 9B: 92 mg of L-7-(3-methoxy-2-benzothienylglycylamido)-3-methyl-3-cephem-4-carboxylic acid.

The benzothienylglycyl cephalosporins provided by this invention are valuable antibiotic substances, or intermediates therefor. The compounds are particularly effective against a wide variety of gram-positive bacilli, and are especially useful in the treatment of upper respiratory infections and similar diseases caused by *S. aureus*, *S. pyogenes*, and the like. The compounds are also effective in the treatment of diseases caused by anaerobic cocci such as *Peptostreptococcus anaerobius*, *Peptostrept. intermedius*, *Peptostrept. productus*, *Peptococcus osaccharolyticus*, *P. prevotii*, *P. avaerobius*, *Propionibacterium acnes*, *Fusobacterium necrophorum*, and the like.

The antibacterial activity of several compounds of the invention has been determined in standard in vitro agar dilution assays against a variety of gram positive and gram negative microorganisms. The following Tables present typical minimum inhibitory concentrations (MIC's) in μg/ml for several compounds of the invention when evaluated against the indicated microorganisms. MIC's for several known compounds are also presented for comparison.

TABLE I

| | | | | Agar Dilution MIC (μg/ml) | | | | | |
| | | Ampi- | Cepha- | Compound of | | | | | |
| Organism | Strain | cillin | lexin | Ex. 2 | Ex. 5 | Ex. 7A | Ex. 7B | Ex. 9A | Ex. 9B |
|---|---|---|---|---|---|---|---|---|---|
| *Staph. aureus* | X1.1 | 0.25 | 4 | 0.5 | 0.25 | 0.5 | 2 | 4 | 16 |
| | V41 | 32 | 128 | 32 | 16 | 2 | 16 | 64 | >128 |
| | X400 | 128 | 128 | 64 | 64 | 32 | 128 | >128 | >128 |
| | S13E | 64 | 128 | 32 | 8 | 2 | 16 | 64 | >128 |
| *Staph. epi* | EPI1 | 8 | 32 | 4 | 2 | 2 | 8 | 32 | 128 |
| | 222 | 0.25 | 8 | 1 | 0.5 | 1 | 4 | 8 | 32 |
| Strep. A | C203 | 0.03 | 0.5 | 0.125 | 0.06 | 0.25 | 0.5 | 1 | 4 |
| Strep. PN | PARK | 0.03 | 2 | 0.5 | 0.25 | 0.5 | 2 | 4 | 32 |
| Strep. D | X66 | 4 | 128 | | | 32 | >128 | >128 | >128 |
| | 2041 | 2 | 128 | | | 32 | 128 | 128 | >128 |
| *H. influ.* | C.L. | 0.5 | 8 | 2 | 16 | 32 | 64 | 64 | >128 |
| | 76 | 16 | 8 | 0.5 | 4 | 4 | 4 | 32 | 64 |
| *E. coli* | N10 | 8 | 8 | | | >128 | >128 | >128 | >128 |
| | EC14 | 4 | 4 | | | >128 | >128 | 128 | >128 |
| | TEM | 128 | 8 | | | >128 | >128 | >128 | >128 |
| Klebsiella | X26 | 16 | 4 | 32 | 2 | 8 | 32 | 32 | >128 |
| | KAE | 128 | 128 | | | >128 | >128 | >128 | >128 |
| | X68 | 16 | 8 | | | >128 | >128 | >128 | >128 |

TABLE II

| | | Expanded Spectrum MIC (μg/ml) | | | |
| | | Compound of | | | |
| Organism | Strain | Ex. 2 | Ex. 5 | Ex. 7A | Ex. 9A |
|---|---|---|---|---|---|
| *Staph. epi* | EPI1 | 4 | 4 | 4 | 4 |
| | 270 | 1 | 0.5 | 2 | 1 |
| | 219 | 0.25 | 0.5 | 0.5 | 0.25 |
| | 269 | 1 | 2 | 1 | 1 |
| | 285 | 0.5 | 1 | 1 | 0.5 |
| | 286 | 0.25 | 0.25 | 0.25 | 0.25 |
| *Staph. aureus* | S224 | 0.25 | 0.5 | 0.5 | 0.25 |
| | S225 | 0.25 | 0.5 | 0.5 | 0.25 |
| | S226 | 0.5 | 0.5 | 0.5 | 0.5 |
| | S227 | 0.25 | 0.5 | 0.5 | 0.25 |
| | S228 | 0.25 | 0.5 | 0.5 | 0.25 |
| | S229 | 0.5 | 1 | 0.5 | 0.5 |
| | S230 | 0.25 | 0.5 | 0.5 | 0.25 |
| | S231 | 0.25 | 0.25 | 0.25 | 0.25 |
| | S234 | 0.5 | 1 | 0.5 | 0.5 |
| | S237 | 0.5 | 0.5 | 0.5 | 0.5 |
| | S238 | 1 | 1 | 0.5 | 1 |
| | 239 | 0.5 | 0.5 | 0.5 | 0.5 |
| *H. influ.* | C.L. | 32 | 16 | 32 | |
| | 76 | 8 | 8 | 16 | |
| | HESS | 32 | 16 | 32 | |
| | STEL | >64 | >64 | 32 | |
| | 312 | 8 | 4 | 16 | |
| | R465 | 32 | 16 | 16 | |
| | 1930 | 8 | 16 | 16 | |
| | 4842 | 8 | 4 | 8 | |
| | 1683 | 1 | 4 | 4 | |
| | M366 | >64 | >64 | 32 | |
| | M370 | 4 | 4 | 8 | |
| | M371 | 2 | 4 | 8 | |
| | 105 | 2 | 4 | 8 | |
| | 158 | 8 | 4 | 8 | |
| | 164 | 2 | 4 | 8 | |
| | 171 | 4 | 16 | 8 | |
| | 169 | 8 | 16 | 8 | |

The data in the above Tables clearly demonstrate the potent antibacterial activity possessed by the compounds of this invention. In addition to possessing potent antibacterial activity against a wide variety of microorganisms, particularly gram positive organisms and anaerobes, the compounds of this invention also have very favorable pharmacokinetics in animals. The compounds of the invention also have good stability to $\beta$-lactamases.

The favorable pharmacokinetics of the compounds provided by this invention, coupled with their excellent antibacterial activity and oral absorption, make them particularly attractive agents for the treatment of a number of diseases of bacterial origin. The compounds are especially well suited for the treatment of outpatients, and especially for subjects suffering from mild upper respiratory infections caused by gram positive microorganisms.

The treatment of animals suffering from bacterial diseases, or suspected of developing a bacterial infection, is thus another embodiment of this invention. The antibacterial method of treatment provided by this invention will be practiced by administering an antibacterially effective amount of a benzothienylglycyl cephalosporin antibiotic as defined herein to an animal in need of treatment. The method can be practiced therapeutically or prophlactically. The amount of active antibiotic to be administered according to the method will vary depending upon the particular compound selected for use, the severity of the disease being treated or guarded against, the individual undergoing treatment, and related factors commonly encountered with such treatments. Normally, however, the compounds will be administered at a dose of about 0.5 to about 50 mg/kg of animal body weight, and more preferably at a rate of about 1 to about 10 mg/kg. Such amounts will be administered once each day, or more often as needed to treat the particular disease or subject undergoing treatment according to the present method. A typical daily dose for an average adult human will be about 200 to about 500 mg per day.

The antibiotic compounds provided by this invention are active by both the oral and parenteral routes of administration, and accordingly can be formulated for any such desired route of administration. Such formulations constitute yet another embodiment of this invention. The formulations of this invention will comprise from about 0.1 to about 95 percent by weight of an active benzothienylglycyl cephalosporin antibiotic of the invention, admixed with a pharmaceutically acceptable carrier, diluent or excipient therefor. Typical formulations will contain from about 10 to about 60 percent by weight of active ingredient, and more preferably about 20 to about 50 percent.

For convenient oral administration, the compounds can be admixed with any of a number of diluents, excipients and carriers commonly employed in oral formulations, and molded into tablets, pills, troches, or encapsulated into gelatin capsules. Typical carriers, diluents and excipients commonly employed include potato starch, corn starch, sucrose, dextrose, microcrystalline cellulose, dicalcium phosphate, alginic acid, acacia; lubricants such as magnesium stearate; binders such as gum tragacanth or gelatin; and flavoring agents such as peppermint oil, cherry or strawberry flavoring, oil of wintergreen, and the like. The compounds can also be formulated as syrups or elixirs employing common diluents such as a fatty oil, methyl or propylparabens, suitable dyes and flavoring agents. The compounds can also be formulated in the form of a buccal seal, logenze or other suitable device for sustained controlled delivery of the active ingredient over a prolonged period.

The antibiotics of the invention can also be formulated for parenteral administration, for example via the intravenous, intramuscular or subcutaneous routes, as well as the transdermal route. Such compositions normally will contain from about 0.1 to about 20.0 percent by weight of active ingredient. Typical excipients, diluents and carriers for parenteral formulations include isotonic saline, dilute aqueous dextrose, the polyhydric aliphatic alcohols or mixtures thereof, for instance glycerin, propylene glycol, polyethylene glycol, and the like. Parenteral solutions may also contain preservatives such as phenethylalcohol, methyl and propyl parabens, thimerosal and the like. If needed, about 0.05 to about 0.20 percent by weight of an antioxidant such as sodium metabisulfite or sodium bisulfite can also be employed. For intravenous use, preferred formulations will employ an initial concentration down to about 0.05 to about 0.25 mg/ml of active ingredient, and for intramuscular injection, a preferred concentration of active ingredient is about 0.25 to about 0.50 mg/ml.

Examples of typical pharmaceutical formulations contemplated by this invention include the following.

EXAMPLE 10

Formulation of Oral Suspension

| Ingredient | Amount |
|---|---|
| Sodium D-7-(3-chloro-2-benzothienyl)-glycylamido-3-chloro-3-cephem-4-carboxylate | 500 mg |
| Sorbitol solution (70% N.F.) | 40 ml |
| Sodium benzoate | 150 mg |
| Saccharin | 10 mg |
| Cherry flavor | 50 mg |
| Distilled water q s ad | 100 ml |

The sorbitol solution is added to 40 ml of distilled water and the benzothienylglycyl cephalosporin is suspended thereon. The saccharin, sodium benzoate, and flavoring are added and dissolved. The volume is adjusted to 100 ml with distilled water. Each ml of syrup contains 5 mg of the benzothienylglycyl cephalosporin antibiotic. This oral formulation is ideally suited for pediatric use.

EXAMPLE 11

Preparation of 250 mg capsule

| Ingredient | Amount |
|---|---|
| 7-(6-Chloro-2-benzothienyl)glycylamido-3-methyl-3-cephem-4-carboxylic acid | 250 mg |
| Lactose | 150 mg |
| Corn starch | 100 mg |
| | 500 mg |

The ingredients are blended to uniformity and encapsulated into gelatin capsules. Such capsules are orally administered at the rate of about one each day for the treatment of upper respiratory bacterial infections, including pharyngitis and tonsillitis.

EXAMPLE 12

Preparation of Parenteral Solution

In a solution of 700 ml of propylene glycol and 200 ml of distilled water for injection is dissolved 20.0 grams of D-7-(3-methoxy-2-benzothienyl)glycylamido-3-methoxymethyl-3-cephem-4-carboxylic acid, hydrochloride. The pH of the solution is adjusted to 5.5 with hydrochloric acid, and the volume is made up to 1000 ml with distilled water. The formulation is sterilized, filled into 5.0 ml ampoules each containing 2.0 ml (representing 40 mg of active ingredient) and sealed under nitrogen.

I claim:

1. A compound of the formula

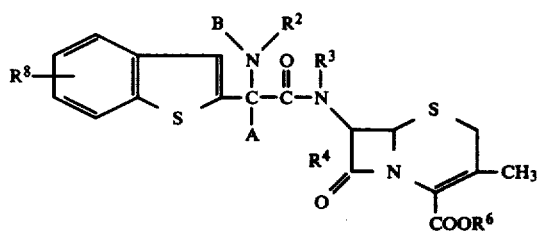

wherein:

$R^8$ is halo;

A and B both are hydrogen, or taken together complete a double bond;

$R^2$ is hydrogen, an amino protecting group, hydroxy, or methoxy, and $R^3$ is hydrogen, or $R^2$ and $R^3$ taken together are

where

M and N independently are $C_1$–$C_4$ alkyl;

$R^4$ is hydrogen, methoxy or methylthio;

$R^6$ is hydrogen, a salt forming cation group, or a carboxy protecting group; and the pharmaceutically acceptable acid addition salts thereof; provided that $R^2$ is hydroxy or methoxy only when A and B complete a double bond, and that A and B both are hydrogen when $R^3$ is other than hydrogen.

2. The compound of claim 1 wherein $R^2$ and $R^3$ are taken together to form

3. The compound of claim 1 wherein A and B are taken together to complete a double bond.

4. The compound of claim 3 wherein $R^2$ is methoxy.

5. The compound of claim 1 wherein A and B both are hydrogen.

6. The compound of claim 5 wherein $R^4$ is hydrogen.

7. The compound of claim 6 wherein $R^6$ is hydrogen or a salt forming cation.

8. The compound of claim 7 wherein $R^8$ is chloro.

9. The compound of claim 8, said compound being D-7-(5-chloro-2-benzothienyl)glycylamido-3-methyl-3-cephem-4-carboxylic acid.

10. The compound of claim 7 wherein $R^8$ is fluoro.

11. A method of treating bacterial infections in animals comprising administering an effective amount of an antibacterial compound of claim 1.

12. The method of claim 11 employing a compound wherein A, B, $R^2$, $R^3$ and $R^4$ all are hydrogen.

13. The method of claim 12 employing a compound wherein $R^6$ is hydrogen or a salt forming cation.

14. The method of claim 13 employing a compound wherein $R^8$ is chloro.

15. The method of claim 14 employing D-7-(5-chloro-2-benzothienyl)glycylamido-3-methyl-3-cephem-4-carboxylic acid.

16. The method of claim 13 employing a compound wherein $R^8$ is fluoro.

17. A pharmaceutical formulation comprising an antibacterially effective amount of a compound of claim 1 admixed with a pharmaceutical carrier, diluent or excipient.

18. The formulation of claim 17 employing a compound wherein A, B, $R^2$, $R^3$ and $R^4$ all are hydrogen.

19. The formulation of claim 18 employing a compound wherein $R^6$ is hydrogen or a salt forming cation.

20. The formulation of claim 19 employing a compound wherein $R^8$ is chloro.

* * * * *